United States Patent
Guyot-Ferréol et al.

(10) Patent No.: US 12,364,652 B2
(45) Date of Patent: Jul. 22, 2025

(54) COMPOSITION FOR DISPERSING A LIPOSOLUBLE COMPOUND IN AN AQUEOUS PHASE

(71) Applicant: SENSIENT COSMETIC TECHNOLOGIES, Saint-Ouen l'Aumone (FR)

(72) Inventors: Véronique Marguerite Suzanne Guyot-Ferréol, La Garenne Colombes (FR); Anthony Degournay, Etouy (FR)

(73) Assignee: SENSIENT COSMETIC TECHNOLOGIES, Saint-Ouen l'Aumone (FR)

( * ) Notice: Subject to any disclaimer, the term of this patent is extended or adjusted under 35 U.S.C. 154(b) by 517 days.

(21) Appl. No.: 17/802,885

(22) PCT Filed: Feb. 26, 2021

(86) PCT No.: PCT/EP2021/054870
§ 371 (c)(1),
(2) Date: Aug. 26, 2022

(87) PCT Pub. No.: WO2021/170817
PCT Pub. Date: Sep. 2, 2021

(65) Prior Publication Data
US 2023/0141605 A1  May 11, 2023

(30) Foreign Application Priority Data
Feb. 27, 2020 (FR) .................................... 2001957

(51) Int. Cl.
*A61K 8/06* (2006.01)
*A61K 8/60* (2006.01)
*A61Q 13/00* (2006.01)

(52) U.S. Cl.
CPC ............... *A61K 8/06* (2013.01); *A61K 8/604* (2013.01); *A61Q 13/00* (2013.01); *A61K 2800/592* (2013.01)

(58) Field of Classification Search
CPC .... A61K 8/604; A61K 2800/592; A61K 8/04; A61K 8/06; A61K 8/37; A61K 2800/262; A61K 8/31; A61K 8/375; A61K 8/442; A61K 8/466
See application file for complete search history.

(56) References Cited

FOREIGN PATENT DOCUMENTS

| DE | 2366376 A1 * | 9/2011 | ............... A61K 8/34 |
| EP | 2 366 376 | 9/2011 | |
| FR | 2 797 764 | 3/2001 | |

OTHER PUBLICATIONS

International Search Report dated Jun. 8, 2021, for PCT/EP2021/054870, 5 pp., including English translation.
Written Opinion of the ISA dated Jun. 8, 2021, for PCT/EP2021/054870, 6 pp.
French Search Report dated Oct. 20, 2020, for FR Application No. 2001957, 2 pp.

* cited by examiner

*Primary Examiner* — Audrea B Coniglio
(74) *Attorney, Agent, or Firm* — NIXON & VANDERHYE

(57) ABSTRACT

The application relates to a dispersant composition, including: at least one alkyl polyglucoside; and a diester of formula (B)

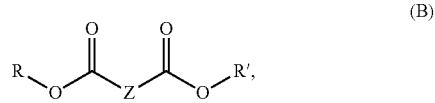

R and R', being the same or different, represent an alkyl group, linear or branched, including from 1 to 10 carbon atoms, and Z is a linear or branched group of formula —$(C_nH_{2n})$—, n being an integer from 1 to 10. The dispersant composition is such that the mass ratio of the proportion by weight of alkyl polyglycoside relative to the proportion by weight of diester of formula (B) is from 7.4 to 18.0.

20 Claims, No Drawings

COMPOSITION FOR DISPERSING A LIPOSOLUBLE COMPOUND IN AN AQUEOUS PHASE

CROSS-REFERENCE TO RELATED APPLICATION(S)

This application is the U.S. national phase of International Application No. PCT/EP2021/054870 filed Feb. 26, 2021, which designated the U.S. and claims priority to FR 2001957 filed Feb. 27, 2020, the entire contents of each of which are hereby incorporated by reference.

BACKGROUND OF THE INVENTION

Field of the Invention

The present invention relates to a dispersant composition for dispersing a liposoluble compound, in particular a fragrance, in an aqueous phase.

Description of the Related Art

The presence of liposoluble compounds in aqueous compositions is widespread in many fields, particularly in the perfumery, cosmetics and cleaning product industries. In the case of fragrance compositions, the liposoluble compound(s) is (are) incorporated into the aqueous composition in particular by means of ethyl alcohol. Aqueous compositions comprising liposoluble compounds also exist in the form of oil-in-water emulsions, in which the liposoluble compound(s) is (are) dispersed by means of surfactants, which are often ethoxylated compounds.

However, the markets for perfumery, cosmetics and cleaning products are moving towards compositions comprising more environmentally-friendly compounds, derived from biomass and/or safer for health. Ethyl alcohol, like the surfactants currently in use, does not meet these criteria.

Furthermore, for a large number of aqueous compositions comprising at least one liposoluble compound, a transparent appearance is required.

There is therefore a need for new compositions to disperse a liposoluble compound in an aqueous phase.

There is also a need for new compositions to obtain a transparent emulsion comprising at least one liposoluble compound.

SUMMARY OF THE INVENTION

One of the aims of the present invention is therefore to propose a dispersant composition based on natural compounds, biodegradable and/or derived from renewable biomasses, which makes it possible to disperse at least one liposoluble compound in an aqueous composition.

Another aim of the present invention is to propose a dispersant composition making it possible to obtain a transparent emulsion comprising at least one liposoluble compound, with the lowest possible mass ratio of dispersant composition to liposoluble compound. The aim is to minimise the amount of dispersant composition in the emulsion, in order to limit costs and/or to avoid possible side effects.

To this end, the aim of the invention is to provide a dispersant composition comprising:
at least one alkyl polyglucoside, and
a diester of formula (B)

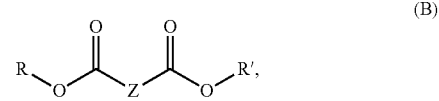

in which R and R', which may be identical or different, represent a linear or branched alkyl group comprising from 1 to 10 carbon atoms, and Z represents a group of formula —$(C_nH_{2n})$—, which may be linear or branched, n being an integer from 1 to 10, said dispersant composition being such that the mass ratio of the proportion by weight of alkyl polyglycoside to the proportion by weight of diester of formula (B) is from 7.4 to 18.0.

The invention also relates to an emulsion comprising
an aqueous phase, and
a dispersed phase comprising at least one liposoluble compound having a log P value strictly greater than 0, the emulsion comprising a dispersant composition according to the invention.

The invention also relates to the use of the dispersant composition according to the invention to improve the transparency of an emulsion comprising an aqueous phase and a dispersed phase comprising at least one liposoluble compound having a log P value strictly greater than 0.

The invention also relates to the use of the dispersant composition according to the invention for dispersing a liposoluble compound having a log P value strictly greater than 0 in an aqueous composition.

The inventors have found that a dispersant composition comprising the combination of at least one alkyl polyglycoside and a diester of formula (B) makes it possible to disperse at least one liposoluble compound in an aqueous phase and to obtain a transparent emulsion at a mass ratio of the sum of the masses of alkyl polyglycoside and of the diester of formula (B) relative to the mass of the liposoluble compound(s) which is lower than the mass ratio:
of the mass of alkyl polyglycoside relative to the mass of the liposoluble compound(s) of a diester-free composition of formula (B), and
of the mass of diester of formula (B) relative to the mass of the liposoluble compound(s) of a composition free of alkyl polyglycoside.

"Mass of the liposoluble compound(s)" means the mass of the liposoluble compound when there is only one, or the sum of the masses of the liposoluble compounds when there are a plurality.

Advantageously, in order to obtain a transparent emulsion by dispersing a liposoluble compound within an aqueous phase, it is therefore possible to use a lower proportion by weight of dispersant composition according to the invention than:
the proportion by weight of alkyl polyglycoside that would be required if this dispersant were used alone, and
the proportion by weight of diester of formula (B) that would be required if this dispersant were used alone.

Surprisingly, the inventors have found that there is a synergistic effect between the alkyl polyglycoside(s) and the diester of formula (B) with respect to the dispersion of at least one liposoluble compound in an aqueous phase.

In the present application, the compounds are referred to by their INCI name.

An alkyl polyglycoside is a polymer comprising a polyglycoside chain comprising glycoside units in which at least one hydroxyl function of at least one of the glycoside units is O-alkylated.

Preferably, the polyglycoside chain comprises (or consists of) glucose and/or pentose units. An alkyl polyglycoside is in particular an alkyl polyglucoside or an alkyl polypentoside.

Preferably, the alkyl polyglycoside is an alkyl polyglucoside.

Preferably, the alkyl polyglycoside is a C4-C14, preferably C8-C10 alkyl polyglycoside. The alkyl polyglycoside then comprises a polyglycoside chain in which at least one hydroxyl function of at least one of the glycoside units is O-alkylated by a linear or branched alkyl comprising from 4 to 14 carbon atoms, preferably from 8 to 10 carbon atoms.

In the present application, the expression "from X to Y" means "is greater than or equal to X and is less than or equal to Y".

In a preferred embodiment, the alkyl polyglycoside is caprylyl/capryl wheat bran/straw glycosides, coco-glucoside or caprylyl/capryl glucoside or a mixture thereof, preferably coco-glucoside or caprylyl/capryl glucoside.

Caprylyl/capryl wheat bran/straw glycosides is the INCI name for the product obtained by glycosylation between a blend of caprylyl and capryl alcohols, with the monosaccharides derived from the hydrolyzed wheat bran and wheat straw.

Hereafter, the alkyl polyglycoside will be referred to as "alkyl polyglycoside" or "dispersant A".

Preferably, in the diester of formula (B), the group Z is a linear alkyl group of formula —$(CH_2)_n$—.

In formula (B), n is an integer from 1 to 10, preferably n is an integer from 1 to 8, advantageously n is an integer from 1 to 4.

Preferably, in the diester of formula (B), n is an integer equal to 1 or 4, advantageously n is equal to 4.

Preferably, in formula (B), R and R', which may be identical or different, represent a linear or branched alkyl group comprising from 1 to 5 carbon atoms, preferably comprising 2 or 3 carbon atoms.

Preferably, in formula (B), R and R' are identical and represent an isopropyl group or an ethyl group.

Advantageously, the diester of formula (B) is selected from diisopropyl adipate, diisopropyl malonate and diethyl adipate.

Diisopropyl adipate is the INCI name for the compound with CAS number 6938-94-9. Diisopropyl adipate is also known as "isoadipate", "1,6-bis(1-methylethyl) ester of hexanedioic acid" or "dipropan-2-yl hexanedioate".

Diisopropyl malonate is the compound with CAS number 13195-64-7.

Diethyl adipate is the INCI name for the compound with CAS number 627-93-0.

According to one embodiment of the invention, the diester of formula (B) is diisopropyl adipate.

In a particularly preferred embodiment, the alkyl polyglycoside is coco-glucoside or caprylyl/capryl glucoside and the diester of formula (B) is selected from diisopropyl adipate diisopropyl malonate and diethyl adipate, more preferably the alkyl polyglycoside is coco-glucoside or caprylyl/capryl glucoside and the diester of formula (B) is diisopropyl adipate.

Hereinafter, the diester of formula (B) will be referred to as "diester of formula (B)" or "dispersant B".

Unless otherwise stated, the mass proportions of dispersant are relative to the total mass of the dispersant composition. For example, the proportion by weight of dispersant A is relative to the total mass of the dispersant composition.

The mass ratio A/B is the proportion by weight of A to the proportion by weight of B.

Preferably, in the dispersant composition, the mass ratio A/B of the proportion by weight of dispersant A to the proportion by weight of dispersant B is 9.0 to 15.0, preferably 9.5 to 15.0, more preferably 9.5 to 13.0, more preferably 8 to 13, advantageously 10.0 to 10.5.

According to one embodiment, the dispersant composition further comprises triethyl citrate, the mass ratio of the proportion by weight of alkyl polyglycoside to the proportion by weight of triethyl citrate being from 66.0 to 90.0.

Triethyl citrate is the INCI name for the compound with CAS number 77-93-0.

In the present application, triethyl citrate is referred to as "triethyl citrate" or "dispersant C".

Preferably, the mass ratio A/C of the proportion by weight of dispersant A to the proportion by weight of dispersant C is 66.0 to 80.0, preferably 70.0 to 80.0, advantageously 70.0 to 75.0.

The presence of triethyl citrate in the dispersant composition exacerbates the synergistic effect between the alkyl polyglycoside and the diester of formula (B) with respect to the dispersion of at least one liposoluble compound in an aqueous phase.

Preferably, the mass ratio of the proportion by weight of diester of formula (B) to the proportion by weight of triethyl citrate is 3.2 to 8.0.

Preferably, the mass ratio B/C of the proportion by weight of dispersant B to the proportion by weight of dispersant C is 6.5 to 7.5, preferably 6.8 to 7.2, advantageously equal to 7.0.

Such values of B/C mass ratio make it possible to improve the performance of the dispersant composition with respect to the dispersion of at least one liposoluble compound in an aqueous solution. Such values of B/C mass ratio allow to decrease the dispersant/liposoluble compound mass ratio used in the emulsion while obtaining a transparent emulsion.

In a preferred dispersant composition:
the mass ratio of the proportion by weight of dispersant A to the proportion by weight of dispersant B is 7.4 to 18.0,
the mass ratio of the proportion by weight of dispersant A to the proportion by weight of dispersant C is 66.0 to 90.0, and
the mass ratio of the proportion by weight of dispersant B to the proportion by weight of dispersant C is 3.2 to 8.0.

In a preferred dispersant composition:
the mass ratio of the proportion by weight of dispersant A to the proportion by weight of dispersant B is 10.0 to 10.5,
the mass ratio of the proportion by weight of dispersant A to the proportion by weight of dispersant C is 70.0 to 75.0, and
the mass ratio of the proportion by weight of dispersant B to the proportion by weight of dispersant C is 6.8 to 7.2.

In a preferred dispersant composition:
the mass ratio of the proportion by weight of dispersant A to the proportion by weight of dispersant B is 7.2 to 0.7,
the mass ratio of the proportion by weight of dispersant A to the proportion by weight of dispersant C is 7.2 to 0.1, and
the mass ratio of the proportion by weight of dispersant B to the proportion by weight of dispersant C is 0.7 to 0.1.

Advantageously, the dispersant composition according to the invention is natural according to ISO 16128-2:2017.

According to the invention, a natural composition is a composition in which the proportion by weight of dry extract of natural compounds is greater than or equal to 50%.

"Natural compound" means a compound with a natural origin index greater than or equal to 1 according to ISO 16128-2:2017.

For example, caprylyl/capryl wheat bran/straw glycosides generally have a natural origin index of 99.6.

Triethyl citrate has a natural origin index of 1.

Indeed, triethyl citrate is preferably obtained by esterification of citric acid and ethanol, the citric acid and ethanol being obtained by fermentation of carbohydrate raw materials from renewable biomasses.

A natural dispersant composition has a lower environmental impact.

The invention also relates to an emulsion comprising
an aqueous phase, and
a dispersed phase comprising at least one liposoluble compound with a log P value strictly greater than 0,
the emulsion comprising a dispersant composition according to the invention.

Log P, also called Log Kow, is a measure of the solubility of chemical compounds between octanol and water (octanol/water partition coefficient).

The log P is equal to the logarithm of the ratio of the concentrations of the test substance in octanol and in water. log P=log($C_{oct}/C_{eau}$) This value allows us to understand the hydrophilic or hydrophobic (liposoluble) nature of a molecule. Indeed, if the log P is positive, this expresses the fact that the molecule under consideration is more soluble in octanol than in water, which reflects its liposoluble nature, and vice versa.

According to the invention, a liposoluble compound has a log P value strictly greater than 0, preferably greater than or equal to 1.

Advantageously, the emulsion according to the invention is transparent.

Indeed, the inventors have discovered that the combination of alkyl polyglycoside with a diester of formula (B) makes it possible to obtain an emulsion comprising at least one liposoluble compound while being transparent.

"Transparent" means an emulsion with an optical density of 0.0 to 0.1 at 600 nanometres (nm) and 25° C.

If the optical density of the emulsion at 600 nm is strictly greater than 0.1, the emulsion is considered cloudy.

The optical density of the emulsion at 600 nm is determined using a Konica Minolta spectrophotometer model CM-5 in transmission mode for a wavelength of 600 nm.

The emulsion to be measured is placed in a dedicated tank. Thanks to a monochromator, a monochromatic light with a wavelength of 600 nm passes through the emulsion in the tank. The value of the intensity transmitted through the sample then provides the optical density data.

Preferably, the emulsion according to the invention is transparent at temperatures of 4° C. to 45° C.

Preferably, the liposoluble compound is chosen from the list consisting of odorant molecules, fragrances, emollient compounds, ultraviolet filters and cosmetic actives.

Advantageously, the liposoluble compound is selected from the list consisting of menthyl lactate, ethylhexyl salicylate, phenethyl alcohol, cis-tetrahydro-2-isobutyl-4-methylpyran-4-ol, trans-tetrahydro-2-isobutyl-4-methylpyran-4-ol (Florosa, EC No. 405-040-6, CAS No. 63500-71-0), benzyl acetate, linalool, Hedione®, gamma-decalactone, dimethyl myrcetone, Verdox®, hexyl cinnamal, amyl salicylate and Habanolide®.

Preferably, in the emulsion, the mass ratio of the sum of the mass proportions of alkyl polyglycoside, diester of formula (B), and triethyl citrate if any, to the proportion by weight of liposoluble compound, is less than or equal to 25, preferably less than or equal to 20.

The mass proportions within the emulsion are relative to the total mass of the emulsion.

Advantageously, in the emulsion, the mass ratio "(A+B+possible C)/liposoluble compound" of the sum of the mass proportions of dispersant A, dispersant B and possible dispersant C, relative to the proportion by weight of liposoluble compound, is from 3 to 20, preferably from 3 to 15, advantageously from 3 to 10.

Preferably, in the emulsion, the proportion by weight of the liposoluble compound is from 1% to 5%, preferably from 2% to 5%, based on the total mass of the emulsion.

The presence of the dispersant composition in the emulsion makes it possible to obtain an emulsion comprising a high proportion by weight of liposoluble compound while remaining transparent.

In one embodiment, the dispersed phase of the emulsion is in the form of droplets having an average diameter as measured by dynamic light scattering of 10 nanometers to 20 nanometers.

Droplet size can be measured by dynamic light scattering (DLS). Such a large droplet size of the dispersed phase of the emulsion allows the emulsion to be transparent because the sizes are smaller than the wavelength of light.

Preferably, the emulsion according to the invention is a cosmetic composition, a perfumery product composition, or a household cleaning product composition.

The invention also relates to the use of the dispersant composition according to the invention to improve the transparency of an emulsion comprising an aqueous phase and a dispersed phase comprising at least one liposoluble compound having a log P value strictly greater than 0.

The invention also relates to the use of the dispersant composition according to the invention for dispersing a liposoluble compound having a log P value strictly greater than 0 in an aqueous composition.

DESCRIPTION OF THE PREFERRED EMBODIMENTS

Further advantages of the present invention will become apparent from the following illustrative examples.

Example 1: Synergistic Effect of Dispersants

In example 1, dispersant A is caprylyl/capryl wheat bran/straw glycosides, dispersant B is diisopropyl adipate and dispersant C is triethyl citrate.

The ability of the dispersants in the composition to disperse liposoluble compounds in an aqueous phase was evaluated using one of the following three fragrances as the liposoluble compound: "Almond", "Floral Aquatic" and "Musky" (Sensient Fragrance) according to the following protocol:

1) the liposoluble compound and the dispersant(s) are blended. Depending on the quantities involved, this blending can be done either with a spatula, or on a magnetic stirring plate, or by stirring with a propeller, frame blade or anchor.

2) demineralised water is gradually added to the liposoluble compound-dispersant(s) blend.

This method is not limited to the preparation of transparent emulsion according to the invention.

The transparency of each emulsion obtained was determined by measuring their optical density (OD 600) at a wavelength of 600 nm. To perform the optical density measurement of the emulsions, a Konica Minolta spectrophotometer model CM-5 is used in transmission mode at a wavelength of 600 nm.

The emulsion to be measured is placed in a dedicated tank. Thanks to a monochromator, a monochromatic light with a wavelength of 600 nm passes through the emulsion in the tank. The value of the intensity transmitted through the sample then provides the optical density value.

A sample is considered transparent if its optical density is less than or equal to 0.1. The quantities of each dispersant are expressed by proportion by weight relative to the total mass of the emulsion obtained. The quantity of fragrance is expressed by proportion by weight relative to the total mass of the emulsion obtained. For example, emulsion E1 comprises 9% by mass of dispersant A, 1% by mass of dispersant B, 1% by mass of Musky fragrance, the remainder (89% by mass) being water.

The comparative emulsions are designated "EC" and the emulsions according to the invention are designated "E".

These protocols are valid for all the examples below.

|  | Prop. by weight Dispersant A (%) | Prop. by weight Dispersant B (%) | Prop. by weight Dispersant C (%) | Fragrance and prop. by weight (%) | Mass ratio of dispersants (A + B + C)/fragrance | Transparency (DO 600) |
|---|---|---|---|---|---|---|
| EC1 | 10 | — | — | Floral aquatic 1 | 10 | >1 |
| EC2 | 15 | — | — | Floral aquatic 1 | 15 | 0.00 |
| EC3 | 10 | — | — | Musky 1 | 10 | >1 |
| EC4 | 15 | — | — | Musky 1 | 15 | 0.00 |
| EC5 | — | 10 | — | Floral aquatic 1 | 10 | No emulsion |
| EC6 | — | 25 | — | Floral aquatic 1 | 25 | No emulsion |
| EC7 | — | 10 | — | Musky 1 | 10 | No emulsion |
| EC8 | — | 25 | — | Musky 1 | 25 | No emulsion |
| EC9 | — | — | 10 | Floral aquatic 1 | 10 | No emulsion |
| EC11 | — | — | 25 | Floral aquatic 1 | 25 | No emulsion |
| EC12 | — | — | 10 | Musky 1 | 10 | No emulsion |
| EC13 | — | — | 25 | Musky 1 | 25 | No emulsion |
| E1 | 9 | 1 | — | Musky 1 | 10 | 0.00 |
| E2 | 9 | 1 | — | Floral aquatic 1 | 10 | 0.003 |
| E3 | 7.2 | 0.7 | 0.1 | Floral aquatic 1 | 8 | 0.00 |
| E4 | 9.0 | 0.875 | 0.125 | Floral aquatic 1 | 10 | 0.00 |
| E5 | 7.2 | 0.7 | 0.1 | Musky 1 | 8 | 0.00 |
| E6 | 9.0 | 0.875 | 0.125 | Musky 1 | 10 | 0.00 |

Neither dispersant B (diisopropyl adipate) nor dispersant C (triethyl citrate), when used alone, will produce an emulsion, regardless of the dispersant/fragrance ratio used (10 or 25) and regardless of the fragrance (EC5-EC9 and EC11-EC13 emulsions).

Dispersant A (caprylyl/capryl wheat bran/straw glycosides), when used alone, produces a transparent emulsion when used in a high ratio to the fragrance (dispersant A/fragrance ratio of 15–emulsions EC2 and EC4), but the emulsion is no longer transparent when the dispersant/fragrance ratio is reduced (dispersant A/fragrance ratio of 10–emulsions EC1 and EC3).

On the other hand, when dispersant A is combined with dispersant B (emulsions E1 and E2), a transparent emulsion is obtained for a dispersant A+B/parfum ratio equal to 10.

A synergistic effect is therefore observed between dispersant A and dispersant B (compare EC1 with E1 and EC3 with E2).

This synergistic effect is exacerbated by using a combination of the 3 dispersants A+B+C. The combination of the 3 dispersants A+B+C makes it possible to obtain a transparent emulsion with a lower proportion of dispersants A+B+C/fragrance (dispersant A+B+C/fragrance ratio of 8/1–emulsions E3 and E5) than in the case where only dispersants A and B are present (dispersant A+B/fragrance ratio of 10/1–emulsions E1 and E2).

Example 2: Evaluation of the Influence of the Mass Ratios A/B, A/C and B/C on the Performance of Dispersant Compositions For all emulsions in example 2, dispersant A is caprylyl/capryl wheat bran/straw glycosides, dispersant B is diisopropyl adipate and dispersant C is triethyl citrate.

All the emulsions in example 2 include 1% by mass of "Musky" fragrance.

| | Prop. by weight Dispersant A (%) | Prop. by weight Dispersant B (%) | Prop. by weight Dispersant C (%) | Mass ratio A/B | Mass ratio A/C | Mass ratio B/C | Mass ratio of dispersants (A + B + C)/ fragrance | Transparency (DO 600) |
|---|---|---|---|---|---|---|---|---|
| EC14 | 8.0 | 2.0 | — | 4 | — | — | 10 | >1 |
| EC15 | 8.5 | 1.5 | — | 5.67 | — | — | 10 | >1 |
| EC16 | 8.7 | 1.3 | — | 6.69 | — | — | 10 | >1 |
| EC17 | 8.8 | 1.2 | — | 7.33 | — | — | 10 | >1 |
| E7 | 8.9 | 1.1 | — | 8.09 | — | — | 10 | 0.004 |
| E8 | 9 | 1 | — | 9 | — | — | 10 | 0.00 |
| E9 | 9.2 | 0.8 | — | 11.5 | — | — | 10 | 0.002 |
| E10 | 9.4 | 0.6 | — | 15.7 | — | — | 10 | 0.001 |
| EC16 | 9.5 | 0.5 | — | 19 | — | — | 10 | 0.124 |
| EC17 | 9.8 | 0.2 | — | 49 | — | — | 10 | 0.459 |
| E11 | 7.165 | 0.731 | 0.104 | 9.80 | 68.9 | 7 | 8 | 0.001 |
| E5 | 7.2 | 0.7 | 0.1 | 10.29 | 72.0 | 7 | 8 | 0.00 |
| E12 | 7.28 | 0.630 | 0.090 | 11.56 | 80.9 | 7 | 8 | 0.00 |
| E13 | 7.344 | 0.574 | 0.082 | 12.79 | 89.6 | 7 | 8 | 0.003 |
| EC18 | 7.574 | 0.320 | 0.105 | 23.67 | 72.1 | 3.05 | 8 | 0.52 |
| EC19 | 7.496 | 0.4 | 0.104 | 18.74 | 72.1 | 3.85 | 8 | 0.129 |
| E14 | 7.417 | 0.48 | 0.103 | 15.45 | 72 | 4.66 | 8 | 0.005 |

Example 3: Evaluation of the Influence of the Dispersant/Liposoluble Compound Mass Ratio at Constant Proportion by Weight of Liposoluble Compound on the Performance of Dispersant Compositions All the emulsions in Example 3 were prepared from a dispersant composition comprising dispersants A, B and C in the following proportions by mass: 7.2/0.7/0.1, or from a comparative dispersant composition comprising only dispersant A.

For all emulsions in example 3, dispersant A is caprylyl/capryl wheat bran/straw glycosides, dispersant B is diisopropyl adipate and dispersant C is triethyl citrate.

A range of liposoluble compounds was tested, including the three fragrances "Almond", "Floral Aquatic" and "Musky" used in examples 1 and 2, but also the following compounds (referred to by their INCI name or trade name): Menthyl lactate (Symrise), Ethylhexyl salicylate (DSM), Phenethyl alcohol (Sensient Fragance), Florosa (Sensient Fragance), Benzyl acetate (Sensient Fragance), Linalool (Sensient Fragance), Hedione® (Sensient Fragance), Gamma-decalactone (Sensient Fragance), Dimethyl myrcetone (Sensient Fragance, Verdox® (Sensient Fragance), Hexyl cinnamal (Sensient Fragance), Amyl salicylate (Sensient Fragance) and Habanolide® (Sensient Fragance).

All the emulsions in example 3 include 1% by mass of liposoluble compound.

| Dispersant(s) | liposoluble compound and prop. by weight (%) | Mass ratio of dispersant(s) to liposoluble compound | Transparency (DO 600) |
|---|---|---|---|
| A + B + C | Floral aquatic fragrance 1 | 8/1 | 0.00 |
| A | Floral aquatic fragrance 1 | 10/1 | >1 |
| A + B + C | Musky fragrance 1 | 8/1 | 0.00 |
| A | Musky fragrance 1 | 10/1 | >1 |
| A + B + C | Hedione ® 1 | 15/1 | 0.00 |
| A | Hedione ® 1 | 15/1 | 0.156 |
| A + B + C | Gamma decalactone 1 | 15/1 | 0.013 |
| A | Gamma decalactone 1 | 15/1 | 0.217 |
| A + B + C | Habanolide ® 1 | 10/1 | 0.001 |
| A | Habanolide ® 1 | 10/1 | >1 |
| A + B + C | Almond fragrance 1 | 3/1 | 0.019 |

-continued

| Dispersant(s) | liposoluble compound and prop. by weight (%) | Mass ratio of dispersant(s) to liposoluble compound | Transparency (DO 600) |
|---|---|---|---|
| A + B + C | Almond fragrance 1 | 5/1 | 0.00 |
| A + B + C | Menthyl lactate 1 | 19/1 | 0.00 |
| A + B + C | Ethylhexyl salicylate 1 | 20/1 | 0.00 |
| A + B + C | Phenethyl alcohol 1 | 10/1 | 0.021 |
| A + B + C | Florosa 1 | 5/1 | 0.002 |
| A + B + C | Benzyl acetate 1 | 20/1 | 0.003 |
| A + B + C | Linalool 1 | 20/1 | 0.009 |
| A + B + C | Dimethyl myrcetone 1 | 10/1 | 0.001 |
| A + B + C | Verdox ® 1 | 10/1 | 0.002 |
| A + B + C | Hexyl cinnamal 1 | 15/1 | 0.00 |
| A + B + C | Amyl salicylate 1 | 15/1 | 0.004 |

The dispersant composition according to the invention makes it possible to obtain transparent emulsions comprising a wide variety of liposoluble compounds.

The synergistic effect between dispersants A, B and C mentioned in Example 1 is also observed with these other liposoluble compounds: Compared to the use of dispersant A alone, the use of a dispersant composition according to the invention requires a smaller amount of dispersants to obtain a transparent emulsion comprising a liposoluble compound. In other words, for certain dispersant(s)/liposoluble compound ratios, dispersant A alone does not make it possible to obtain a transparent emulsion, unlike the dispersant composition according to the invention.

Example 4: Evaluation of the Influence of the Proportion of Liposoluble Compound on the Performance of Dispersant Compositions All the emulsions in Example 4 were prepared from a dispersant composition comprising dispersants A, B and C in the following proportions by mass: 7.2/0.7/0.1.

For all emulsions in example 4, dispersant A is caprylyl/capryl wheat bran/straw glycosides, dispersant B is diisopropyl adipate and dispersant C is triethyl citrate.

The proportion by weight of liposoluble compound in the emulsion was increased to 2%, 3% and 4%. The proportion by weight of dispersants in the emulsion was also progressively increased in order to determine the minimum mass ratio of dispersants to liposoluble compound to obtain a transparent emulsion comprising 2%, 3% or 4% by mass of said liposoluble compound.

| Prop. by weight of dispersants (A + B + C) (in %) | Liposoluble compound and prop. by weight (%) | Mass ratio of dispersants to liposoluble compound | Transparency (DO 600) |
|---|---|---|---|
| 3 | Almond fragrance 1 | 3/1 | 0.00 |
| 6 | Almond fragrance 2 | 6/2 = 3/1 | 0.03 |
| 8 | Floral aquatic fragrance 1 | 8/1 | 0.00 |
| 18 | Floral aquatic fragrance 2 | 18/2 = 9/1 | 0.002 |
| 28 | Floral aquatic fragrance 3 | 28/3 | 0.007 |
| 7 | Musky fragrance 1 | 7/1 | 0.001 |
| 8 | Musky fragrance 1 | 8/1 | 0.00 |
| 16 | Musky fragrance 2 | 16/2 | 0.08 |
| 28 | Musky fragrance 3 | 28/3 | 0.01 |
| 38 | Musky fragrance 4 | 38/4 | 0.006 |
| 19 | Menthyl lactate 1 | 19/1 | 0.00 |
| 36 | Menthyl lactate 2 | 36/2 | 0.00 |
| 57 | Menthyl lactate 3 | 57/3 | 0.00 |
| 76 | Menthyl lactate 4 | 76/4 | 0.00 |

The results obtained show that the use of a dispersant composition according to the invention makes it possible to obtain emulsions comprising a proportion by weight of up to 4% by mass of liposoluble compound which are transparent.

Example 5: Influence of the Nature of the Diester of Formula B

In example 5, dispersant A is caprylyl/capryl wheat bran/straw glycosides, dispersant C is triethyl citrate, and dispersant B is the following formula:

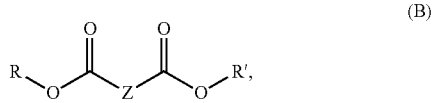

(B)

with R and R', which may be identical or different, representing a linear or branched alkyl group comprising from 1 to 10 carbon atoms, and Z representing a group of formula —(C$_n$H$_{2n}$)—, which may be linear or branched, n being an integer from 1 to 10.

All the emulsions in Example 5 were prepared from a dispersant composition comprising dispersants A, B and C in the following proportions by mass: 7.2/0.7/0.1.

All emulsions in example 5 comprise 1% by weight of "Musky" fragrance, and a mass ratio (A+B+C)/fragrance of 8:1.

| | Nature of dispersant B | Transparency (DO 600) |
|---|---|---|
| E15 | Diisopropyl adipate | 0.00 |
| E16 | Diisopropyl malonate | 0.01 |
| E17 | Diethyl adipate | 0.01 |

The invention claimed is:

1. A dispersant composition comprising:
   at least one alkyl polyglucoside, and
   a diester of formula (B)

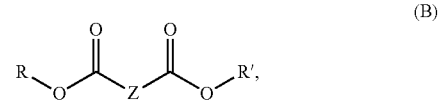

(B)

in which R and R', being the same or different, represent an alkyl group, linear or branched, comprising from 1 to 10 carbon atoms, and Z is a linear or branched group of formula (C$_n$H$_{2n}$)—, n being an integer from 1 to 10, the dispersant composition being such that the mass ratio of the proportion by weight of alkyl polyglycoside relative to the proportion by weight of diester of formula (B) is from 7.4 to 18.0.

2. The composition according to claim 1, wherein the alkyl polyglycoside is a C4-C14 alkyl polyglycoside.

3. The composition according to claim 1, in which R and R', which may be identical or different, represent a linear or branched alkyl group comprising from 1 to 5 carbon atoms.

4. The dispersant composition according to claim 1, further comprising triethyl citrate, the mass ratio of the proportion by weight of alkyl polyglycoside to the proportion by weight of triethyl citrate being from 66.0 to 90.0.

5. The dispersant composition according to claim 4, wherein the mass ratio of the proportion by weight of diester of formula (B) to the proportion by weight of triethyl citrate is from 3.2 to 8.0.

6. An emulsion comprising:
   an aqueous phase, and
   a dispersed phase comprising at least one liposoluble compound with a log P value strictly greater than 0,
   the emulsion comprising a dispersant composition according to claim 1.

7. The emulsion according to claim 6, wherein the mass ratio of the sum of the mass proportions of alkyl polyglycoside, diester of formula (B), and triethyl citrate if any, to the proportion by weight of liposoluble compound, is less than or equal to 25.

8. The emulsion according to claim 6, wherein the proportion by weight of the liposoluble compound is from 1% to 5% based on the total weight of the emulsion.

9. The emulsion according to claim 6, the dispersed phase of which is in the form of droplets having an average diameter as measured by dynamic light scattering of from 10 nanometers to 20 nanometers.

10. A method for dispersing a liposoluble compound having a log P value strictly greater than 0 in an aqueous composition, the method comprising adding the dispersant composition according to claim 1 to said aqueous composition.

11. The composition according to claim 2, wherein the alkyl polyglycoside is a C8-C10 alkyl polyglycoside.

12. The composition according to claim 3, in which R and R', which may be identical or different, represent a linear or branched alkyl group comprising 2 or 3 carbon atoms.

13. The emulsion according to claim 7, wherein the mass ratio of the sum of the mass proportions of alkyl polyglycoside, diester of formula (B), and triethyl citrate if any, to the proportion by weight of liposoluble compound, is less than or equal to 20.

14. The emulsion according to claim 8, wherein the proportion by weight of the liposoluble compound is from 2% to 5%, based on the total weight of the emulsion.

15. The dispersant composition according to claim 2, further comprising triethyl citrate, the mass ratio of the proportion by weight of alkyl polyglycoside to the proportion by weight of triethyl citrate being from 66.0 to 90.0.

16. The dispersant composition according to claim 3, further comprising triethyl citrate, the mass ratio of the proportion by weight of alkyl polyglycoside to the proportion by weight of triethyl citrate being from 66.0 to 90.0.

17. An emulsion comprising:
an aqueous phase, and
a dispersed phase comprising at least one liposoluble compound with a log P value strictly greater than 0, the emulsion comprising a dispersant composition according to claim 2.

18. An emulsion comprising:
an aqueous phase, and
a dispersed phase comprising at least one liposoluble compound with a log P value strictly greater than 0, the emulsion comprising a dispersant composition according to claim 3.

19. An emulsion comprising:
an aqueous phase, and
a dispersed phase comprising at least one liposoluble compound with a log P value strictly greater than 0, the emulsion comprising a dispersant composition according to claim 4.

20. An emulsion comprising:
an aqueous phase, and
a dispersed phase comprising at least one liposoluble compound with a log P value strictly greater than 0, the emulsion comprising a dispersant composition according to claim 5.

\* \* \* \* \*